United States Patent [19]

Jackson et al.

[11] E Patent Number: Re. 33,509

[45] Reissued Date of Patent: Dec. 25, 1990

[54] BROMINATED SUCROSE DERIVATIVES, COMPOSITIONS AND METHODS OF USE

[75] Inventors: Graham Jackson, Caversham; Michael R. Jenner, Welcombe; Riaz A. Khan, Sonning, all of England

[73] Assignee: Tate & Lyle p.l.c., Great Britain

[21] Appl. No.: 346,632

[22] Filed: May 3, 1989

Related U.S. Patent Documents

Reissue of:

[64] Patent No.: 4,473,546
Issued: Sep. 25, 1984
Appl. No.: 379,331
Filed: May 18, 1982

[30] Foreign Application Priority Data

May 22, 1981 [GB] United Kingdom ..... 8115838

[51] Int. Cl.[5] ..... C07H 5/02; A23G 3/30; A61K 7/16

[52] U.S. Cl. ..... 536/122; 424/48; 424/49; 514/777; 426/3; 426/658

[58] Field of Search ..... 536/122; 426/658, 3; 424/48, 49; 514/777

[56] References Cited

U.S. PATENT DOCUMENTS

| | | | |
|---|---|---|---|
| 4,148,887 | 4/1979 | Smith | 424/180 |
| 4,228,150 | 10/1980 | Robyt et al. | 424/180 |
| 4,335,100 | 6/1982 | Robyt et al. | 536/122 |
| 4,343,934 | 8/1982 | Jenner et al. | 536/122 |
| 4,405,654 | 9/1983 | Lee | 426/658 |
| 4,435,440 | 3/1984 | Hough et al. | 514/777 |
| 4,801,700 | 1/1989 | Tully et al. | 536/122 |

FOREIGN PATENT DOCUMENTS

| | | | |
|---|---|---|---|
| 1543167 | 12/1976 | United Kingdom | 424/180 |

*Primary Examiner*—Ronald W. Griffin
*Attorney, Agent, or Firm*—Ostrolenk, Faber, Gerb & Soffen

[57] ABSTRACT

Compounds of the general formula (I) are potent sweeteners, especially 4,1′,6′-tribromo-4,1′,6′-trideoxygalactosucrose:

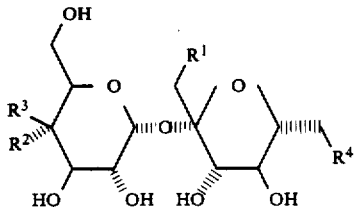

(I)

in which

R′ represents a chlorine or bromine atom;

$R^2$ and $R^3$ respectively represent a hydroxy group and a hydrogen atom or a hydrogen atom and a chlorine or bromine atom;

$R^4$ represents a chlorine or bromine atom; at least one of R′, $R^3$ and $R^4$ representing a bromine atom.

14 Claims, No Drawings

BROMINATED SUCROSE DERIVATIVES, COMPOSITIONS AND METHODS OF USE

Matter enclosed in heavy brackets [ ] appears in the original patent but forms no part of this reissue specification; matter printed in italics indicates the additions made by reissue.

This invention relates to the certain new bromo-substituted sucrose derivatives and to their use as sweeteners.

British Patent Specification No. 1,543,167 of Tate & Lyle Limited discloses and claims the use of a number of chlorine-substituted sucrose derivatives as powerful sweeteners. Those compounds were the first sucrose derivatives to exhibit a sweetness considerably greater than the sweetness of sucrose itself. Many sucrose derivatives are known in which one or more hydroxy groups is replaced by another radical. In every case, the derivatives is either less sweet than sucrose or (in a small number of cases) of the same order as that of sucrose. The chlorosucrose derivatives of British Patent No. 1,543,167 were particularly interesting in that they generally possessed a sweetness of the order of several hundred times that of sucrose. The sweet chlorosucroses of British Patent No. 1,543,167 are defined by the general formula

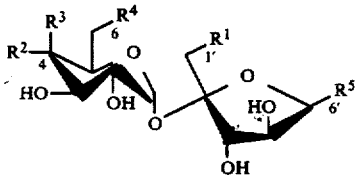

in which $R^1$ represents a hydroxy group or a chlorine atom;

$R^2$ and $R^3$ respectively represent a hydroxy group and a hydrogen atom, a chlorine atom and a hydrogen atom, or a hydrogen atom and a chlorine atom;

$R^4$ represents a hydroxy group; or, in at least two of $R^1$, $R^2$, $R^3$ and $R^5$ represents chlorine atoms, $R^4$ represents a hydroxy group or a chlorine atom; and $R^5$ represents a hydroxy group or a chlorine atom; provided that at least one of $R^1$, $R^2$ and $R^3$ represents a chlorine atom.

A particularly important chlorosucrose sweetener is 4,1',6'-trichloro-4,1',6'-trideoxygalatosucrose, also known as TGS.

Many analogous compounds have been prepared, in which the chlorine atoms have been replaced by other radicals. The sweetness of the chlorosucrose derivatives is still not understood. Various theories have been proposed in order to explain the sweetness of sweet compounds, notably by Shallenberger. Regardless of detailed theoretical considerations, it might be supposed that replacement of the chlorine substituents by other substituents of a similar polarity and/or size might lead to molecules having similar taste characteristics. However, a considerable number of sucrose derivatives have been tested containing substituents such as ester groups or amide groups, but no sweet compounds have been observed.

It might be supposed that simply replacing one or more chlorine atoms in chlorosucrose sweeteners by other halogen atoms would give similar sweeteners.

However, as in the case of many physiologically active compounds, replacement of chlorine by another halogen can be undesirable. For example, 4,6'-dichloro-4,6'-dideoxygalatosucrose has a sweetness about 4,6'-difluoro derivatice is found to have a sweetness only 4 times that of sucrose. Similarly, iodination at the 4-,1'- and 6'-positions yeilds a product only one fifth as sweet as TGS.

It is thus a matter of some surprise that replacement of certain chlorine atoms by bromine atoms would lead to a compound which is strongly sweet. Bromine and chlorine radicals are very different in size and the differences in atomic radii and polarity would lead to sucrose derivatives of considerably different characteristics. In spite of this, some bromosucrose derivatives are potent sweetening agents.

According to the present invention, therefore we provide a compound of the general formula (I)

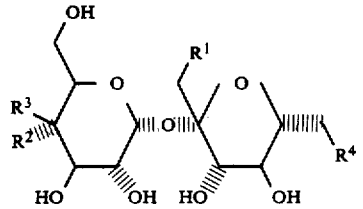

(I)

in which $R^1$ represents a chlorine or bromine atom;

$R^2$ and $R^3$ respectively represents a hydroxy group and a hydrogen atom or a hydrogen atom and a chlorine or bromine atom;

$R^4$ represents a chlorine or bromine atom; at least one of $R^1$, $R^3$ and $R^4$ representing a bromine atom.

Particularly preferred are the compounds of the general formula (I), in which at least one and more preferably both of $R^1$ and $R^4$ represents bromine atoms. The compound of choice is 4,1',6'-tribromo-4,1',6'-trideoxygalactosucrose, otherwise more properly known as 1,6-dibromo-1,6-dideoxy-β-D-fructofuranoxyl 4-bromo-4-deoxy-α-D-galactopyranoside.

We further provide a method of sweetening a substance comprising incorporating therein a compound of the formula (I) as defined above, especially 4,1',6'-tribromo-4,1',6'-trideoxygalactosucrose. We also provide an ingestible product or oral composition containing a compound of the formula (I) as defined above, especially 4,1',6'-tribromo-4,1',6'-trideoxy-galactosucrose.

The term "ingestible product" used herein means a product which in the ordinary course of use is intended to be swallowed, for instance a foodstuff or beverage or an orally administered pharmaceutical composition. The "oral composition" means a composition which in the originary course of use is not intended to be ingested as such, but is taken into the mouth for the treatment of the throat or buccal cavity, for instance a toothpaste, toothpowder, mouthwash, gargle, troche, dental lotion or chewing gum. The term "sweetening composition" means the composition which is not itself taken orally, either to be ingested or held in the mouth, but instead is intended to be added to other ingestible products or oral compositions to render them sweet, or to increase their sweetness.

The bromo derivatives of formula (I) according to the present invention may be used in the same manner as the chloro sucrose sweeteners.

In general, the bromo derivatives of the general formula (I) defined above are very sweet. When at least one of R' and $R^4$ represent bromine atoms, the derivatives are each at least as sweet as the corresponding chloro-analogue. When R' and $R^3$, represent bromine atoms, the sweetness exceeds that of the chloro-analogues. Examples of this are given in the following table, which records the sweetness as compared with surcrose at a dilution of about 8% by weight:-

| $R^1$ | $R^3$ | $R^4$ | approximate sweetness × sucrose |
|---|---|---|---|
| Br | Br | Br | 800 |
| Br | Cl | Br | 800 |
| Cl | Br | Cl | 375 |
| Br | H | Br | 80 |
| Cl | Cl | Cl | 600 |
| Cl | H | Cl | 75 |

Thus, it will be seen that the tribromo derivative is approximately 800 times as sweet as sucrose (at a dilution of 8%) and thus the quantity of the tribromo compound used will, in general, be about 800 times less than the equivalent amount of sucrose needed for the required degree of sweetness. If desired, additional components can be added, e.g. components to alter the "mouthfeel" of the product.

Sweetening compositions maybe formulated by mixing the bromo derivative of formula (I) with an extender or carrier comprising any suitable vehicle for formulation into a convenient product, e.g. granules, tablets or a solution in a dropper pack. The extender or carrier may thus include, e.g. conventional water-dispersible tabletting ingredients such as starch, lactose and sucrose itself; low density bulking agents to provide granular sweetening compositions having a volume per unit sweetness equivalent to that of sucrose, e.g. spray dried maltodextrins; and aqueous solutions containing adjuvents such as stabilizing agents, colouring agents and viscosity-adjusting agents.

Beverages, such as soft drinks, containing the bromo derivative of formula (I) may be formulated either as sugar-free dietetic products, or "sugar-reduced" products containing the minimum amount of sugar required by law. The invention also comprises within its scope concentrates for dilution, e.g. bottling syrups, fruit squashes and instant desserts and drinks.

The compounds of the general formula (I) can, in general, be prepared by methods analogous to those used for the preparation of the chlorine-substituted compounds of British Patent No. 1,543,167.

In particular, there is provided a method of preparing a compound of the general formula (I), as defined above, comprising reacting a compound of the general formula (II)

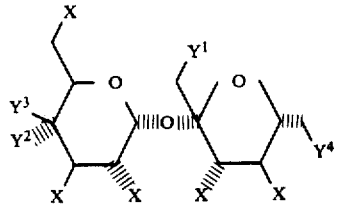

(II)

in which the substituents X, which may be the same or different, each represent a protected hydroxy group;

$Y^1$ and $Y^4$ each represent a chlorine or bromine atom, a hydroxy group, a protected hydroxy group or a leaving group displaceable by a halide ion; and $Y^2$ represents a hydroxy or protected hydroxy group or a leaving group displacable by a halide ion and $Y^3$ represents a hydrogen atom; or $Y^2$ represents a hydrogen atom and $Y^3$ represents a chlorine or bromine atom; at least one of $Y^1$ $Y^2$ and $Y^4$ representing a hydroxy group or leaving group; with (a) a brominating reagent, when at least one of $Y^1$, $Y^2$ and $Y^4$ represents a hydroxy group and the remainder represent chlorine or bromine atoms or protected hydroxy groups;

(b) a chlorinating agent, when one or two of $Y^1$, $Y^2$ and $Y^4$ represents a hydroxy group and the remainder represent bromine atoms or protected hydroxy groups;

(c) a source of bromide ions, when at least one of $Y^1$, $Y^2$ and $Y^4$ represents a leaving group and the remainder represent chloride or bromide atoms or protected hydroxy groups; or (d) a source of chloride ions, when one or two of $Y^1$, $Y^2$ and $Y^4$ represents a leaving group and the remainder represent bromine atoms or protected hydroxy groups.

One general method involves protection of the hydroxy groups of a sucrose molecule in positions other than the 1'-,6'-, and optionally 4- positions and then treating the molecule with the appropriate halogenating reagent. Where a mixed chloro- and bromo-substituted derivative is required, it is necessary to halogenate sequentially by introducing the first halogen in those positions where it is required, hydroxy groups in the remaining positions being protected where necessary, and then introducing the other halogens having first deprotected the required positions. Suitable protecting groups include esters such as aliphatic carboxylic esters, and cyclic esters, such as isopropylidenedioxy groups. Compounds of the general formula (I) in which all of the halogen substituents are the same are preferable for their ease of preparation. Thus, e.g., 4,1',6'-tribromo-4,1',6'-trideoxygalactosucrose can be prepared from the known sucrose 2,3,6,3',4'-pentaacetate, e.g. by treatment with a triarylphosphine and carbon tetrabromide.

An alternative method involves the displacement of a suitable leaving group by a bromide ion. Typical leaving groups include hydrocarbonsulphonyl ester groups, e.g. the methanesulphonyl ester group. Thus, e.g. the tribromo derivative above can also be prepared by reacting the known 4,1',6'-tri-O-methanesulphonylsucrose pentaacetate with lithium bromide in a polar aprotic solvent such as hexamethylphosphoric triamide.

The following examples illustrate the invention further:

EXAMPLE 1

4,1',6'-Tribromo-4,1',6'-trideoxygalactosucrose 4,1',6'-tri-O-methanesulphonylsucrose pentaacetate was prepared according to the method of Hough and Mufti (Carbohydrate Research 29 (1973) 291-296). The pentaacetate (5 g) was dissolved in hexamethylphosphorictriamide (100 ml) and was treated with lithium bromide (5 g) at 90° C. for 10 days. The reaction mixture was worked up by being poured into ice/water and the resulting precipitate was filtered off and dissolved in diethyl ether. The ether solution was then dried over sodium sulphate and concentrated to a solid. This solid material was then reacted with an acetic anhydride-pyridine mixture (5 ml in 50 ml) and the reaction mixture was again evaporated to dryness. The fully acetylated product was then purified by elution through a silica gel column using diethyl ether-light petroleum (1:1). The structure of the resulting 4,1',6'-tribromo-4,1',6'-trideoxygalactosucrose pentaacetate was confirmed by $^1$H-nmr and mass spectrometry.

The tribromopentaaceta (1 g) in methanol (10 ml) was treated with sodium methoxide until a pH of 9 was achieved. After 4 hours at room temperature, the reaction mixture was examined by t.l.c. (dichloromethanemethanol 4:1) to reveal a single slow-moving product. The solution was neutralized with Amberlyst 15 ($H^{30}$) ion-exchange resin, filtered and concentrated to dryness to yield 4,1',6'-tribromo-4,1',6'-trideoxygalactosucrose (0.65 g 88%, $[\alpha]_D^+ +75.2°$ (c, 1.3 acetone).

EXAMPLE 2

4,1',6'-Tribromo-4,1',6'-trideoxygalactosucrose 2,3,6,3',4'-penta-O-acetylsucrose was prepared according to the method of McKeown, Serenius and Hayward, (Canadian J. Chem 35 (1957) 28–36). The pentaacetate (27.6 g) and triphenylphosphine (78.6 g 6 molar equivalents) were dissolved in pyridine (300 ml) at room temperature and then the mixture was cooled to 0° C. Carbon tetrabromide (50 g, 3 molar equivalents) was then added with stirring and the mixture became dark. The mixture was then heated at 75° C. for 1½ hours and then methanol (50 ml was added and the resulting solution was evaporated to a syrup. This syrup was dissolved in dichloromethane (200 ml) and the resulting solution was washed successively with dilute hydrochloric acid, water and aqueous sodium bicarbonate to neutrality. The dichloromethane solution was then dried over anhydrous sodium sulphate and concentrated to dryness and the residue was stirred with diethyl ether (200 ml). A crystalline precipitate of triphenylphosphine oxide was filtered off, the filtrate was concentrated and the product was crystallised from ethanol to give 4,1',6'-tribromo-4,1',6'-trideoxygalactosucrose pentaacetate (18.5 g, 49%). The structure was confirmed by $^1$Hnmr:

4.84 (d, $J_{1,2}$ 3.5 Hz, H-1);
5.37 (q, $J_{2,3}$ 10.0 Hz, H-1);
5.19 (q, $J_{3,4}$ 10.0 Hz, H-3);
5.86 (q, $J_{4,5}$ 1.5 Hz, H-4);
4.77 (d, $J_{3',4'}$6.0 Hz, H-3');
5.11 (t, $J_{4',5'}$6.0 Hz, H-4');
8.3–8.41 (15H, 5-OAc)

Mass spectral data [(a) indicates a 1:2:1 triplet due to hexopyranosyl cation and (b) indicated a 1:1 doublet due to tetopyranosyl cations]:

M/e: τ371/373/375 (a),
351/353 (b),
311/313/315 (a),
291/293 (b),
231/233 (b),
189/191 (b).

4,1',6'-tribromo-4,1',6'-trideoxygalactosucrose pentaacetate (5 g) was dissolved in methanol (50 ml) and treated with 1N sodium methoxide to pH 9. After 4 hours at room temperature, the solution was neutralized with Amberlyst 15 (H+) resin, filtered and concentrated to dryness to give 4,1',6'-trideoxygalactosucrose as a dry syrup, $[\alpha]_D^{20}+75.2°$ (c, 1.3, acetone). In later Examples, the compound is referred to as TBS

EXAMPLE 3

4-Bromo-1',6'-dichloro-4,1',6'-trideoxygalactosucrose (1)

2,3,6,3',4'-Penta-O-acetyl-1',1',6'-dichloro-1',6'-dideoxysucrose

A solution of 2,3,6,3',4'-penta-O-acetylsucrose (16.6 g) in pyridine (100 ml) was treated with triphenylphosphine (26.2 g, 4 ME) to give a clear solution at room temperature. After cooling to 0° C., carbon tetrachloride (9.2 g, 2 ME) was added and the stirred mixture heated to 70° for 1.5 h. Tlc revealed a major product corresponding to the required compound. Methanol (20 ml) was added to the cooled reaction mixture which was then evaporated. The residue was dissolved in dichloromethane and this was washed with water, 1M hydrchloric acid, saturated aqueous sodium biucarbonate solution and water, then dried, filtered through charcoal and evaporated. The resulting syrup was stirred with ether for 1 h and the crystalline precipitate of triphenylphosphine oxide was filtered off. The filtrate was evaporated and eluted from a silica gel column using ether-petrol (1:1) to give the 1',6'-dibromo derivative (6.6 g, 37%).

(2) Bromination to give 4-bromo-1',6'-dichloro-4,1',6'-trideoxygalactosucrose penta-acetate A solution of the dichloro derivative (6.6 g) in pyridine (70) was treated with triphenylphosphine (8.7 g, 3 ME), then cooled to 0° C. and carbon tetrabromide (5.6 g, 1.5 ME) added. The reaction mixture was heated to 70° for 2 h after which tlc revealed a single product. Methanol (10 ml) was added to the cooled reaction which was then evaporated. The residue was worked up as described in step (1). 4-Bromo-1',6'-dichloro-4,1',6'-trideoxygalactosucrose penta-acetate was obtained by crystallisation from ethanol and recrystallised to give 5.2 g (71%).

(3) De-acetylation

A solution of the penta-acetate (5.2 g) in methanol (50) ml) was treated with 1M sodium methoxide in methanol to pH and at room temperature for 3 h. The solution was neutralised with Amberlyst 15 [H+] resin, filtered and evaporated to give 3.3 g (95%) of 4-bromo-1',6'-dichloro-4,1',6'-trideoxygalacosucrose as a syrup; $[\alpha]_D^{20}+81.2°$ (c 1.0, $H_2O$).

EXAMPLE 4

4-Chloro-1',6'-dibromo 4,1',6'-trideoxygalactosucrose

A mixture of 2,3,6,3',4'-penta-O-acetylsucrose (50 g) and trityl chloride (100 g) (of ca. 75% purity) in pyridine (400 ml) was heated at 80° for 8 hrs. The reaction mixture was poured into water and the water was then decanted away from the precipitate. The water-washed precipitate was then dissolved in dichloromethane which was washed with 1M HCl, and with saturated aqueous sodium bicarbonate and then dried, filtered through charcoal and evaporated. The residue was taken up in methanol, from which tritanol crystallized. The precipitate was filtered off and the filtrate was evaporated. The residue was then dissolved in pyridine 300 ml and stirred with molecular sieves (0.4 nm) for two hours. The sieves were then filtered off and to the pyridine solution was added triphenylphosphine (50 g, 2 ME) followed by carbon tetrachloride (15 ml, 1.5 ME) at room temperature. The mixture was heated to 70° for 1½ hours and then cooled. Methanol (20 ml) was added and the mixture was evaporated. The residue was dissolved in dichloromethane which was washed with 1M HCl and aqueous sodium bicarbonate and then dried, filtered through charcoal and evaporated. The residue was taken up in ether and the crystalline precipitate of triphenylphosphineoxide was filtered off.

The contents of ether solution were then taken up in glacial acetic acid (750 ml) and heated to about 110°; water (15 ml) was added and the mixture was gently refluxed (about 120°) for 1 hour. It was then evaporated at reduced pressure at under 50° and co-distilled with toluene. Tritanol present in the mixture was crystallized from a methanol solution and the remaining product was then subjected to column chromatography on silica gel using ether as the eluent to give 4-chloro-4-deoxygalactosucrosepentaacetate (6.2 g, 12%).

To a solution of the above pentaacetate (6.2 g, 1 ME) and triphenylphosphine (11.4 g, 4 ME) in pyridine (100 ml) was added, at room temperature, carbon tetrabromide, (7.3 g, 2 ME). This mixture was heated at 80° for 1 hour, cooled and further triphenylphosphine (5.7 g) and carbon tetrabromide (3.7 g) were added to the reaction mixture which was then heated at 80° for a further 1 hour to complete the reaction. The mixture was cooled and methanol (20 ml) was added. The mixture was then evaporated to give a residue which was dissolved in dichloromethane. The solution was washed with 1 HCl and aqueous sodium bicarbonate and then dried, filtered through charcoal and evaporated. The residue was taken up in ether, from which a crystalline precipitate of triphenylphosphine oxide was filtered off. The filtrate was evaporated and residue was dissolved in ethanol which then yielded 5.9 grams (80%) of the 4-chloro-1',6'-dibromo derivative as the pentaacetate in the form of crystals. Recrystallization from ethanol gave 5.1 g of purified pentaacetate.

This material (1.5 g) was deacetylated using sodium methoxide in methanol at pH approximately 9.5 room temperature. The solution was neutralized with Amberlyst 15 $H^+$ resin and then filtered and evaporated to give 4-chloro-1',6'-dibromo-4,1',6'-trideoxygalacosucrose (1.0 g, 95%) $[\alpha]_D^{20}+52.3°$ (c=0.7, $H_2O$) Melting point 87°-93° (Decomp.).

EXAMPLE 5

1',6'-Dibromo 1',6'-dideoxygalactosucrose 2,3,6,3',4'-Penta-O-acetyl sucrose (13.8 g) was dibrominated in a manner analogous to that of Example 4 using 26.4 g (4 ME) of triphenyl phosphine and about 16.6 g, (2 ME) of carbon tetrabromide in pyridine (100 ml) at 70°. The progress of the reaction was followed by t.l.c. and the product isolated and purified as in Example 4 to yield 6.7 g (40%) of the pentaacetate which was deacetylated as before to give 4.1 g of the product, recrystallised from ethanol/ethyl acetate/ether to give 2.8 g (41%). $[\alpha]_D^{20}+71.1°$ (c=0.4, $H_2O$).

EXAMPLE 6

Sweetening tablets for beverages

Each tablet contains TBS 5 mg, together with a dispersible tablet base (ca. 60 mg) containing sucrose, gum arabic and magnesium stearate, and is equivalent in sweetness to about 4.5 g sucrose.

EXAMPLE 7

Bulked Sweetener

A bulked sweetener having the same sweetness as an equivalent volume of sucrose (granulated sugar) is prepared by mixing the following ingredients and spray-drying to a bulk density of 0.2 g/cc:

Maltodextrin solution containing
dry weight: 222.2 g
TBS: 1.25 g

The resulting composition has a sweetening power equivalent to approximately 2 kilograms of sugar.

EXAMPLE 8

Reduced calorie cola drink containing sugar

Ingredients to prepare 100 ml bottling syrup:
TBS: 50 mg
Sugar: 60 g
Benzoic acid: 35 mg
Phosphoric acid (con.): 1 ml
Cola flavour: 1.1 ml
Colour: ad lib
Make up to 100 ml with mineral water.

This syrup may then be added in 25 ml doses to 225 ml aliquots of carbonated chilled mineral water.

EXAMPLE 9

Carbonated low calorie lemonade (sugar free)

Ingredients to prepare 100 ml syrup:
TBS: 65 mg
Benzoic acid: 35 mg
Citric acid (dry base): 1.67 g
Lemon essence: 0.8 g
Make up to 100 ml in mineral water.

This syrup can be added in 25 ml doses to 225 ml aliquots of carbonated chilled mineral water.

EXAMPLE 10

Toothpaste

| | % by weight |
|---|---|
| Dibasic calcium phosphate | 50% |
| Glycerol | 20% |
| Sodium lauryl sulphate | 2.5% |
| Spearmint oil | 2.5% |
| Gum tragacanth | 1.0% |
| TBS | 0.02% |
| Water | 23.97% |

The ingredients are mixed to produce a spearmint flavoured toothpaste of acceptable sweetness but free from sugar or saccharin.

EXAMPLE 11

Chewing gum

| | parts by weight |
|---|---|
| Polyvinyl acetate | 20 |
| Butyl phthalylbutylglycolate | 3 |
| Polyisobutylene | 3 |
| Microcrystalline wax | 2 |
| Calcium carbonate | 2 |
| Flavouring/aroma | 1 |
| TBS | 0.045 |

-continued

| | parts by weight |
|---|---|
| Glucose | 10 |

The above chewing gum base can be cut into conventional tablets or strips.

We claim:

1. A compound of the general formula (I)

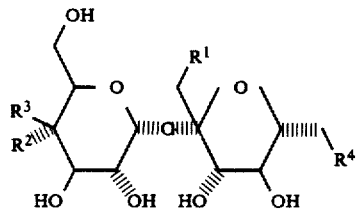

(I)

in which $R^1$ is selected from the group consisting of a chlorine atom and a bromine atom;

$R^2$ and $R^3$ are respectively selected from the group consisting of:

a hydroxy group and hydrogen atom; a hydrogen atom and a chlorine atom; and a hydrogen atom and a bromine atom; and $R^4$ is selected from the group consisting of a chlorine atom and a bromine atom; at least one of $R^1$, $R^3$ and $R^4$ representing a bromine atom, *and when $R^3$ is a chlorine atom, at least one of $R^1$ and $R^4$ is a chlorine atom.*

2. A compound according to claim 1, in which at least one of $R^1$ and $R^4$ represents a bromine atom.

3. A compound according to claim 2, in which both $R^1$ and $R^4$ represent bromine atoms.

4. A compound according to claim 1, namely 1′,6′-dibromo-1′,6′-dideoxy-β-D-fructofuranosyl 4-bromo-4-deoxy-α-D-galactopyranoside.

5. A compound according to claim 1, selected from the group consisting of:

1,6-dichloro-1,6-dideoxy-β-D-fructofuranosyl 4-bromo-4-deoxy-α-D-galactopyranoside;

[1,6-dibromo-1,6-dideoxy-β-D-fructofuranosyl 4-chloro-4-deoxy-α-D-galacetopyranoside;] and 1,6-dibromo-1,6-dideoxy-β-D-fructofuranosyl α-D-glucopyranoside.

6. A method of sweetening an ingestible product or oral composition comprising incorporating therein a sweetening amount of a compound of the general formula (I)

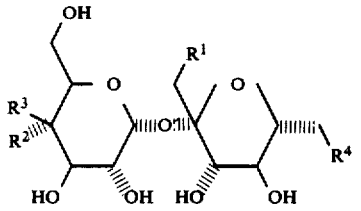

(I)

in which $R^1$ is selected from the group consisting of a chlorine atom and a bromine atom;

$R^2$ and $R^3$ are respectively selected from the group consisting of:

a hydroxy group and a hydrogen atom; a hydrogen atom and a chlorine atom; and a hydrogen atom and a bromine atom; and $R^4$ is selected from the group consisting of a chlorine atom and a bromine atom; at least one of $R^1$, $R^3$ and $R^4$ representing a bromine atom, *and when $R^3$ is a chlorine atom, at least one of $R^1$ and $R^4$ is a chlorine atom.*

7. A method according to claim 6, comprising incorporating therein a compound in which at least one of $R^1$ and $R^4$ represents a bromine atom.

8. An ingestible product or oral composition containing as a sweetening agent in a sweetening amount a compound of the general formula (I)

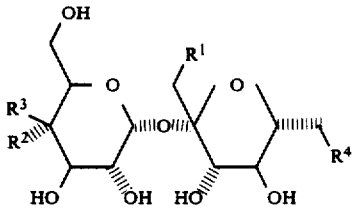

(I)

in which $R^1$ is selected from the group consisting of a chlorine atom and a bromine atom;

$R^2$ and $R^3$ are respectively selected from the group consisting of:

a hydroxy group and a hydrogen atom; a hydrogen atom and a chlorine atom; and a hydrogen atom and a bromine atom; and $R^4$ is selected from the group consisting of a chlorine atom and a bromine atom; at least one of $R^1$, $R^3$ and $R^4$ representing a bromine atom, *and when $R^3$ is a chlorine atom, at least one of $R^1$ and $R^4$ is a chlorine atom,* and and an extender or carrier therefor.

9. A product or composition according to claim 8, containing a compound in which at least one of $R^1$ and $R^4$ represent a bromine atom.

10. A sweetener composition comprising a sweetening amount of a compound of general formula (I)

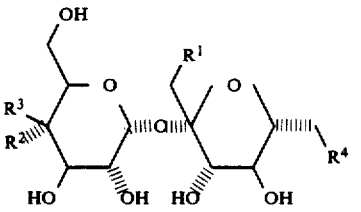

(I)

in which $R^1$ is selected from the group consisting of a chlorine atom and a bromine atom;

$R^2$ and $R^3$ are respectively selected from the group consisting of:

a hydroxy group and a hydrogen atom; a hydrogen atom and a chlorine atom; and a hydrogen atom and a bromine atom; and $R^4$ is selected from the group consisting of a chlorine atom and a bromine atom; at least one of $R^1$, $R^3$ and $R^4$ representing a bromine atom, *and when $R^3$ is a chlorine atom, at least one of $R^1$ and $R^4$ is a chlorine atom,* and and an extender or carrier therefor.

11. A sweetening composition according to claim 10, in which at least one of the $R^1$ and the $R^4$ represent a bromine atom.

12. A sweetening composition according to claim 11, in whch both $R^1$ and $R^4$ represent bromine atoms.

13. A sweetener composition according to claim 10, in which the compound of formula (I) is 1,6-dibromo-1,6-dideoxy-β-D-fructofuranosyl 4-bromo-4-deoxy-α-D-galactopyranoside.

14. A sweetener composition according to claim 10, in which the compound of formula (I) is selected from the group consisting of:

1,6-dichloro-1,6-dideoxy-β-D-fructofuranosyl 4-bromo-4-deoxy-α-D-galactopyranoside; *and*

[1,6-dibromo-1,6-dideoxy-β-D-fructofuranosyl 4-chloro-4-deoxy-α-D-galactopyranoside; or]

1,6-dibromo-1,6-dideoxy-β-D-fructofuranosyl α-D-glucopyranoside.

* * * * *